United States Patent
Allard et al.

(10) Patent No.: US 8,470,002 B2
(45) Date of Patent: Jun. 25, 2013

(54) RESORBABLE RELEASE MECHANISM FOR A SURGICAL TETHER AND METHODS OF USE

(75) Inventors: Randall Noel Allard, Germantown, TN (US); Larry Thomas McBride, Jr., Memphis, TN (US); Shannon Marlece Vittur, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1229 days.

(21) Appl. No.: 11/676,649

(22) Filed: Feb. 20, 2007

(65) Prior Publication Data

US 2008/0234747 A1 Sep. 25, 2008

(51) Int. Cl.
*A61B 17/88* (2006.01)
*A61B 17/70* (2006.01)

(52) U.S. Cl.
USPC ........... 606/279; 606/258; 606/259; 606/262; 606/263

(58) Field of Classification Search
USPC .................. 606/254, 258, 259, 262, 263, 279
See application file for complete search history.

(56) References Cited

U.S. PATENT DOCUMENTS

| | | | |
|---|---|---|---|
| 6,287,308 B1 | 9/2001 | Betz et al. | |
| 6,296,643 B1 | 10/2001 | Hopf et al. | |
| 6,299,613 B1 | 10/2001 | Ogilvie et al. | |
| 6,436,099 B1 | 8/2002 | Drewry et al. | |
| 6,623,484 B2 | 9/2003 | Betz et al. | |
| 6,746,450 B1 | 6/2004 | Wall et al. | |
| 6,761,719 B2 | 7/2004 | Justis et al. | |
| 6,783,527 B2 | 8/2004 | Drewry et al. | |
| 7,018,379 B2 | 3/2006 | Drewry et al. | |
| 2001/0029375 A1 | 10/2001 | Betz et al. | |
| 2003/0023241 A1 | 1/2003 | Drewry et al. | |
| 2005/0203514 A1 | 9/2005 | Jahng et al. | |
| 2005/0216004 A1* | 9/2005 | Schwab .......................... 606/61 |
| 2006/0106381 A1 | 5/2006 | Ferree et al. | |
| 2006/0155279 A1 | 7/2006 | Ogilvie | |
| 2006/0190030 A1 | 8/2006 | To et al. | |
| 2007/0270821 A1* | 11/2007 | Trieu et al. ....................... 606/61 |

FOREIGN PATENT DOCUMENTS

JP 06114067 A * 4/1994

OTHER PUBLICATIONS

Gruca, Adam, The Pathogenesis and Treatment of Idiopathic Scoliosis: A Preliminary Report, 1958; 40:570-584, The Journal of Bone and Joint Surgery, United States.

* cited by examiner

*Primary Examiner* — Eduardo C Robert
*Assistant Examiner* — Julianna N Harvey

(57) ABSTRACT

The present application is directed to tethers and methods of use. The tether is attached with anchors to bony members within the patient. The tether applies a tensile force to the bony members to reduce and/or eliminate the abnormality of the bony members. The tether includes a release mechanism with a resorbable material that initially maintains the tether in a shortened orientation. The release mechanism is eventually releases the tether to a lengthened orientation. The release mechanism may prevent the need for a subsequent surgery to release tension from the tether as the patient grows.

4 Claims, 13 Drawing Sheets

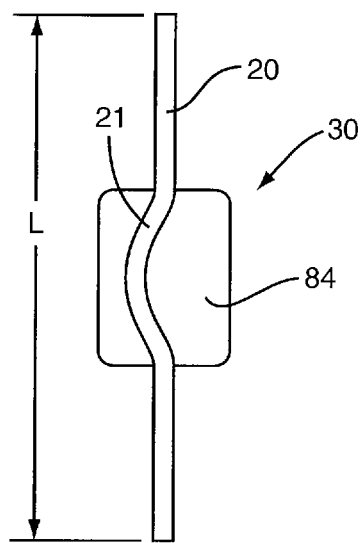 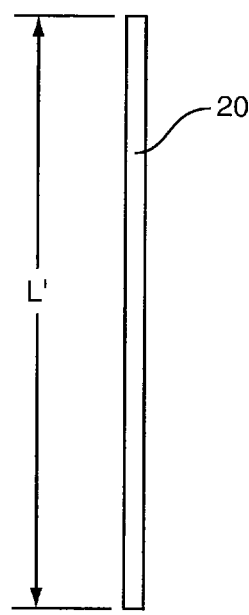
FIG. 5A  FIG. 5B
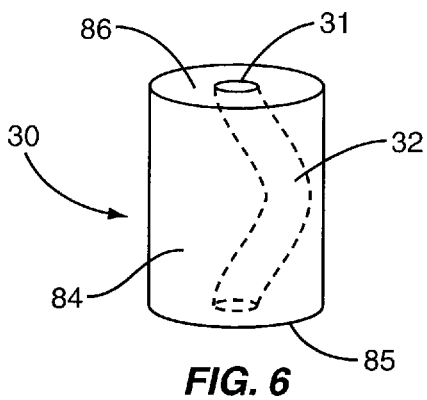
FIG. 6
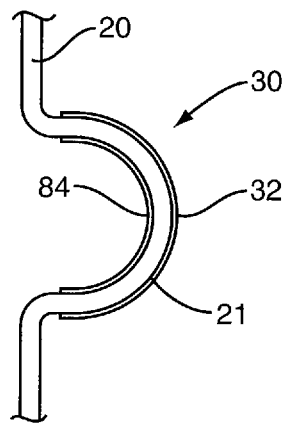 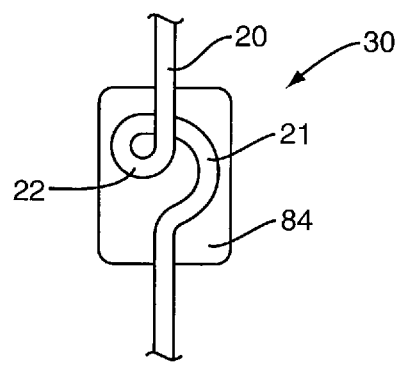
FIG. 7  FIG. 8

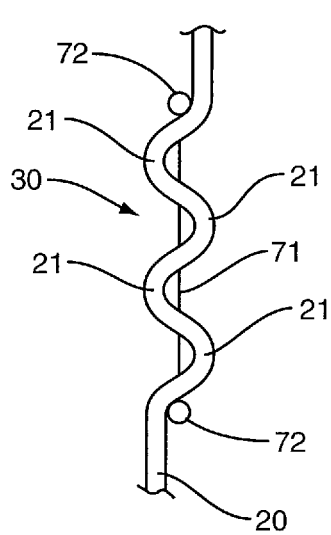
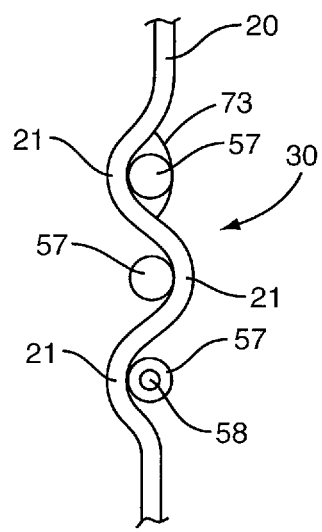
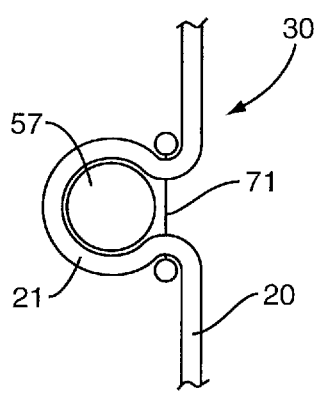
FIG. 19  FIG. 20  FIG. 21
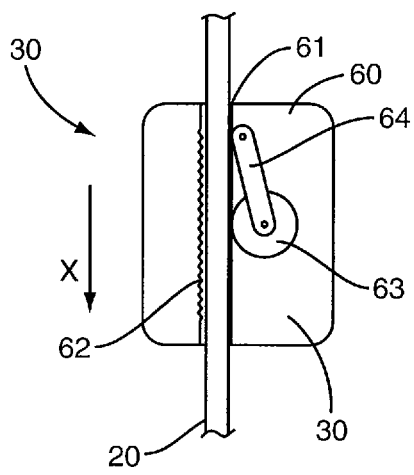
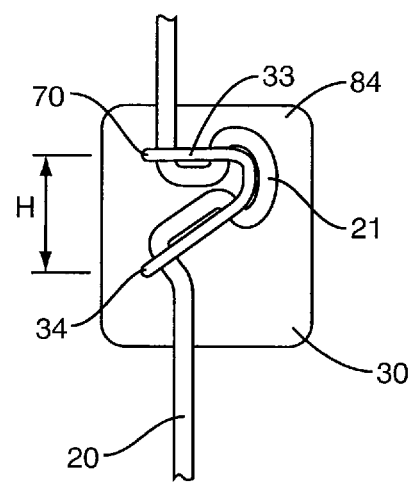
FIG. 22  FIG. 23

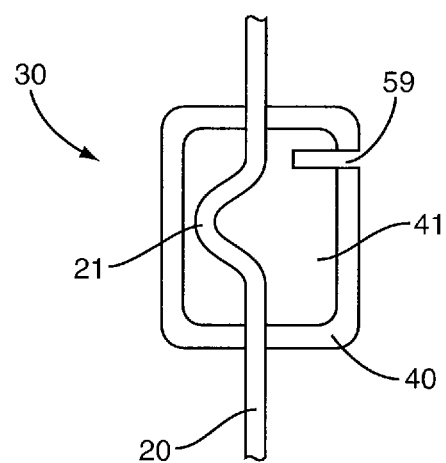
FIG. 24
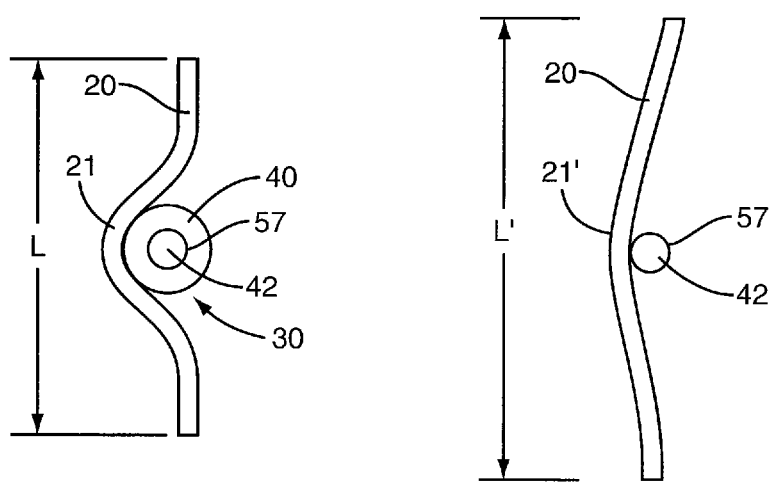
FIG. 25A  FIG. 25B

US 8,470,002 B2

RESORBABLE RELEASE MECHANISM FOR A SURGICAL TETHER AND METHODS OF USE

BACKGROUND

The present application is directed to methods of treating bony members within a patient and, more particularly, to tethers that include a release mechanism that releases after a period of time to release tension on the tether.

Tethers are used in various surgical procedures to apply tension to bony members. One example of a tether is for use in correcting spinal deformities. The spine is divided into four regions comprising the cervical, thoracic, lumbar, and sacrococcygeal regions. Vertebral members of the spine are aligned in a curved configuration that includes a cervical curve, thoracic curve, and lumbosacral curve.

Various deformities may affect the normal alignment and curvature of the vertebral members. Scoliosis is one example of a deformity of the spine in the coronal plane, in the form of an abnormal curvature. While a normal spine presents essentially a straight line in the coronal plane, a scoliotic spine can present various lateral curvatures in the coronal plane. The types of scoliotic deformities include thoracic, thoracolumbar, lumbar or can constitute a double curve in both the thoracic and lumbar regions. Schuermann's kyphosis is another example of a spinal deformity that affects the normal alignment of the vertebral members. One or more tethers may be attached to the vertebral members to reduce and/or eliminate the deformity.

Tethering is often used with patients with growth potential of the bony members including prepubescent children less than ten years old who have yet to experience a growth spurt, and adolescents from 10-12 years old with continued growth potential. One issue with current tethering techniques is the inability of the tether to lengthen as the patient grows. Current tethering techniques require a subsequent surgical procedure to lengthen the tether.

SUMMARY

The present application is directed to tethering systems and methods of use. In one embodiment, the tethering system includes a tether that is connected to first and second bony members. A release mechanism may be operatively connected to the tether and constructed at least in part of a resorbable material that temporarily shortens the tether.

One method of using the tethering system may include attaching the tether with a release mechanism to first and second bony members. After a period of time and while the tethering system is within the patient, the release mechanism may trigger a release of a curved section of the tether to increase the length of the tether between the first and second bony members.

BRIEF DESCRIPTION OF THE DRAWINGS

FIG. 5A is a schematic view of a tether and release mechanism with a first length according to one embodiment.

FIG. 5B is a schematic view of a tether with a second length according to one embodiment.

FIG. 6 is a perspective view of a release mechanism according to one embodiment.

FIG. 7 is a schematic view of a tether within a release mechanism according to one embodiment.

FIG. 8 is a schematic view of a tether within a release mechanism according to one embodiment.

FIG. 19 is a side view of a tether within a release mechanism according to one embodiment.

FIG. 20 is a side view of a tether within a release mechanism according to one embodiment.

FIG. 21 is a side view of a tether within a release mechanism according to one embodiment.

FIG. 22 is a schematic view of a tether within a release mechanism according to one embodiment.

FIG. 23 is a schematic view of a tether within a release mechanism according to one embodiment.

FIG. 24 is a schematic view of a tether within a release mechanism according to one embodiment.

FIG. 25A is a side view of a tether within a release mechanism in a first condition according to one embodiment.

FIG. 25B is a side view of a tether within a release mechanism in a second condition according to one embodiment.

DETAILED DESCRIPTION

Figure 1:
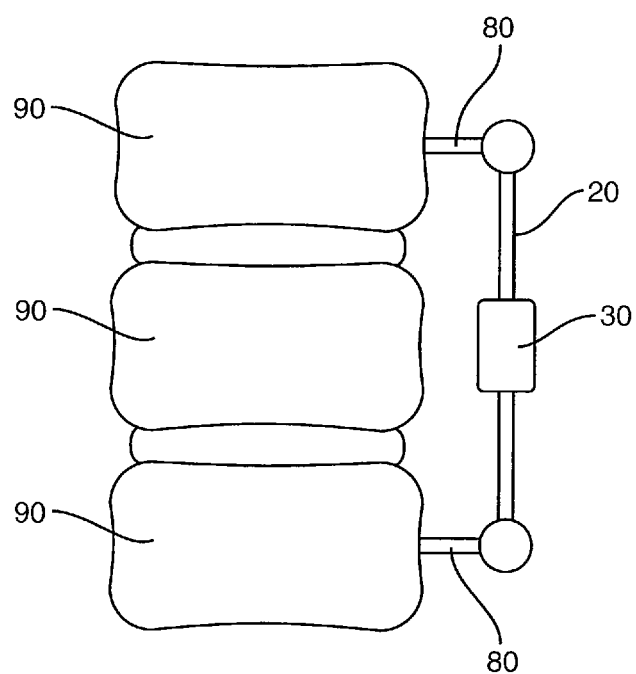
FIG. 1 is a schematic view of a tether with a release mechanism attached by anchors to bony members according to one embodiment.

The present application is directed to methods of using a tether for treating deformities in bony members within a patient. FIG. 1 illustrates a schematic representation of a tethering system 10 that includes a tether 20 attached by anchors 80 to bony members 90. The tether 20 applies a tensile force to the bony members 90 to reduce and/or eliminate the deformity. The tether 20 includes a release mechanism 30 that includes a resorbable material that is absorbed by the body and releases while in the patient causing the tether to increase in length thus reducing an amount of tension on the tether 20. The release mechanism 30 may also reduce potential morbidity associated with growth inhibition on one side of the deformity. The release mechanism 30 may prevent the need for a subsequent surgery to release tension from the tether 20 as the patient grows. The release mechanism 30 may be constructed to release the tether 20 at one instance, or may gradually release the tether over an extended period of time.

Figure 2:
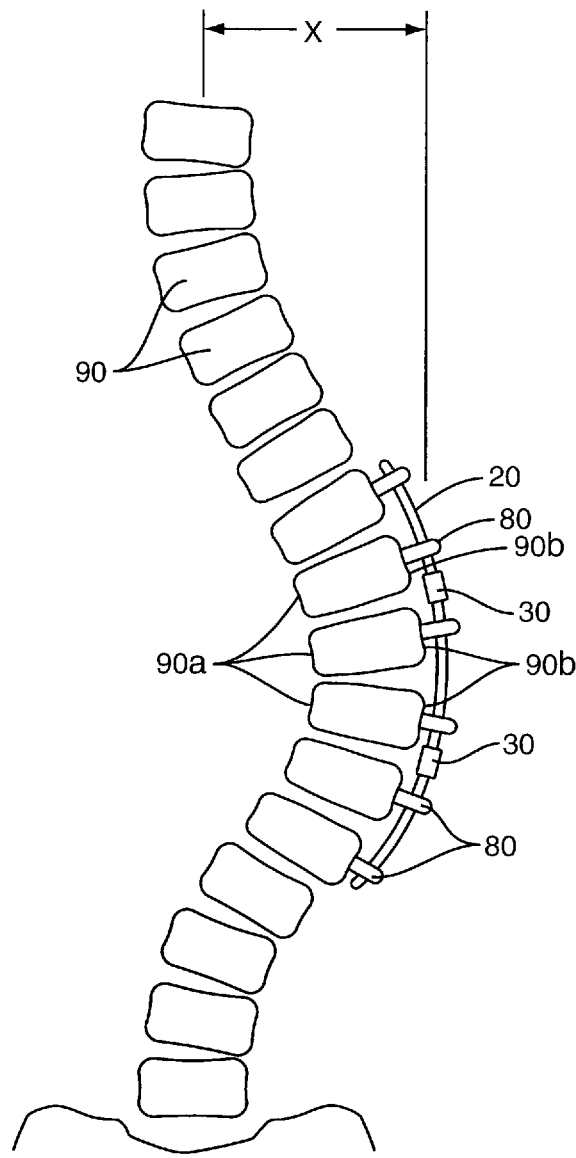
FIG. 2 is a schematic coronal view of a tether with a release mechanism attached to a scoliotic spine according to one embodiment.

The tether 20 may be used for treating a variety of deformities within the patient. FIG. 2 illustrates one context of using a tether 20 for treating a scoliotic spine. This spine has a scoliotic curve with an apex of the curve being offset a distance X from its correct alignment in the coronal plane. The spine is deformed laterally so that the axes of the vertebral members 90 are displaced from the sagittal plane passing through a centerline of the patient. In the area of the lateral deformity, each of the vertebral members 90 includes a concave side 90a and a convex side 90b. In this embodiment, the tether 20 extends along the convex side 90b of two or more adjacent vertebral members 90. Tether 20 minimizes or arrests growth on the convex or "long" side of the spine and allows the concave or "short" side of the spine to grow and catch up with the long side. Alternatively, the tether 20 may treat the spinal deformity by simply preventing further misalignment such as curve progression.

Figure 3:
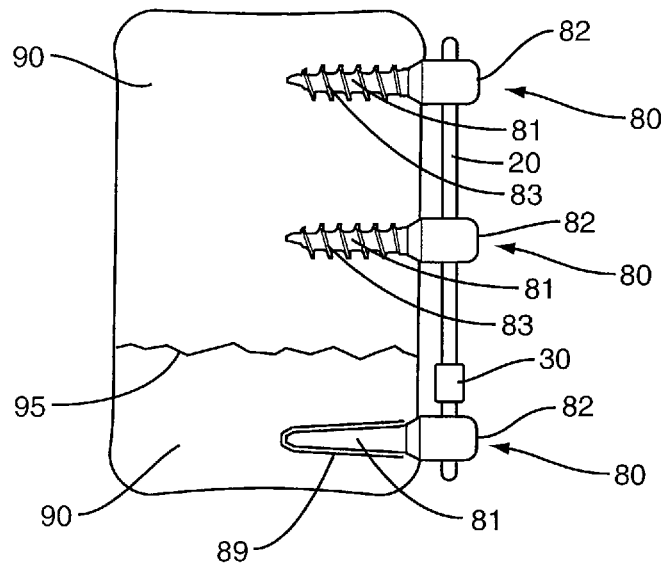
FIG. 3 is a schematic view of anchors that attach the tether to bony members according to one embodiment.

FIG. 3 illustrates another context of use with the tether 20 attached to a fractured bony member 90. One or more anchors 80 are positioned on each side of a fracture 95 to apply tension to the bony members 90. This tension facilitates healing of the fracture 95. The tether 20 may also be used for other procedures, including but not limited to correction of Schuermann's kyphosis, hyperkyphosis, and derotation of a spinal curve.

Various anchors 80 may be used to connect the tether 20 to the bony members 90. FIG. 3 illustrates an embodiment with the anchors 80 including a shaft 81 that extends into the bony member 90. Shaft 81 may further include threads 83 to facilitate insertion and attachment with the bony member 90. An adhesive 89 may be placed on the shaft 81 to increase the attachment with the bony member 90. In one embodiment, the shaft 81 is coated with any number of osteoinductive or osteoconductive materials to enhance attachment as desired. A head 82 extends outward from the shaft 81 and is constructed to receive the tether 20.

A variety of different tethers 20 may be used for treating the spinal deformity. Embodiments include but are not limited to cables, artificial or synthetic strands, rods, plates, and springs. In one embodiment, tether 20 comprises an inner core with an outer sheath. The inner core and outer sheath may be made of a braided polymer such as polyester, polypropylene, or polyethylene. In one specific embodiment, the inner core and outer sheath are both made of polyethylene with the inner core being braided for strength and the outer sheath being braided for abrasion resistance. In one embodiment with the tether 20 being a strand, the strand may be manufactured from a variety of materials, including, but not limited to, conventional biocompatible implant alloys such as titanium, stainless steel, cobalt-chrome alloys, or even shape memory alloys and materials such as nickel-titanium.

Figure 4:
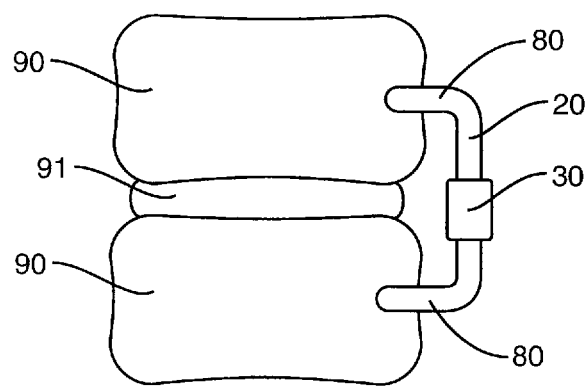
FIG. 4 is a schematic view of anchors that attach the tether to bony members according to one embodiment.

FIG. 4 illustrates another embodiment with a staple that comprises both the tether 20 and anchors 80. Staple is substantially C-shaped with feet that form the anchors 80 that extend into and connect with the bony member 90. A base of the staple extends between the feet to form the tether 20. In this embodiment, anchors 80 and feet 20 are formed as a single member as opposed the embodiment of FIG. 3 with a separate tether 20 and anchors 80. Bony members 90 in this embodiment includes vertebral members that are separated by an intervertebral disc 91.

The release mechanism 30 increases a length of the tether 20 after a period of time of being inserted within the patient. The increase in length results in a decrease in an amount of tension on the tether 20. Release mechanism 30 is made completely or partially from one or more resorbable materials. The release mechanism 30 is initially placed into the patient while the resorbable material or materials are in a first condition to maintain the tether 20 at a shortened orientation. The resorbable material or materials are absorbed over a period of time and change to a second condition that releases the tether 20 to an elongated orientation. The release mechanism 30 may gradually length the tether 20, or may lengthen the tether 20 in a more sudden manner.

The release mechanism 30 may change from the first condition to the second condition in a variety of manners. The change may include a change in shape of the release mechanism, such as from a first shape that shortens the length of the tether 20 to a second shape that lengthens the tether 20. The change may also be a material change such as from a first stiffness to a second, different stiffness. The release mechanism 30 may be programmed to release the tether 20 in accordance with the needs of the patient. This programming may begin the release at a time after being inserted within the patient, and also the extent of the release such as a gradual release over time, or a sudden release.

The release mechanism 30 may be constructed in a variety of different embodiments. FIG. 5A illustrates one embodiment of the release mechanism 30 attached to the tether 20. Release mechanism 30 includes a block 84 that extends around and forms a curved section 21 within the tether 20. In one embodiment, the block 84 is molded to the tether 20. In a first orientation as illustrated in FIG. 5A, the tether 20 with the curved section 21 includes a length L. After the block 84 is absorbed by the body, the curved section 21 is released and the tether 20 expands to a full extended length L' as illustrated in FIG. 5B.

Release of the curved section 21 reduces or removes the amount of tension on the tether 20. The elongation of the tether 20 and associated release in tension may prevent a second surgical procedure that otherwise may be required. The release may also prevent damage to the bony members 90 that may be caused by the application of an excessive amount of tensile force. In one embodiment, an excess tensile force causes the anchors 80 to plow or otherwise extract from the bony members 90.

Release mechanism 30 may be integrally formed with the tether 20. In one embodiment, release mechanism is attached to the tether 20 as part of a molding process. Release mechanism 30 may also be a separate member that is removably attached to the tether 20. FIG. 6 illustrates one embodiment with the release mechanism 30 including a cylindrical block 84 with an aperture 31 that extends through the interior from a first side 85 to a second side 86 and includes a bend 32. In this embodiment, tether 20 is a separate element that is threaded through the aperture 31 prior to or during the surgical procedure. The bend 32 in the aperture 31 forms the curved section 21 in the tether 20.

FIG. 7 illustrates another embodiment with the block 84 being substantially C-shaped. Block 84 is hollow and includes a bend 32 to form the curved section 21 of the tether 20.

FIGS. 6 and 7 illustrate embodiments with the tether 20 maintaining a single-ply or non-coiled orientation. FIG. 8 includes the curved section 21 of the tether forming a coil 22 when the block 84 is in the first condition. FIG. 8 includes a single coil 22 formed in the tether 20, although other embodiments may include two or more coils 22 formed within the release mechanism 20. In one embodiment that includes one or more coils 22, the release mechanism 30 is attached to the tether in a molding process as the coils prevent threading the tether 20 through a coiled aperture 31. In one embodiment, the orientation and/or size of the coil 22 allows for the tether 20 to be threaded. In another embodiment, tether 20 includes a stiffened end that facilitates threading through the coil 22.

Figure 9:
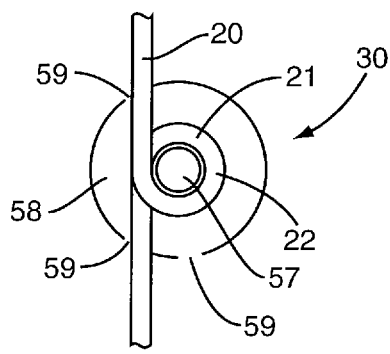
FIG. 9 is a schematic view of a tether within a release mechanism according to one embodiment.

FIG. 9 illustrates another coil embodiment with the release mechanism 30 including a node 57 and an exterior member 58. The tether 20 is wrapped around the node 57 to form a coil 22 that comprises the curved section 21. Node 57 may include a variety of shapes including a cylinder or a sphere. The exterior member 58 is attached to and positions the node 57. In one embodiment, node 57 is constructed of a resorbable material. As the node 57 is absorbed by the body, the coil 22 becomes smaller thus increasing the length of the tether 20. Once the node 57 is completely absorbed, the tether 20 moves to a substantially straight orientation with an increased length as illustrated in FIG. 5B.

Figure 10:
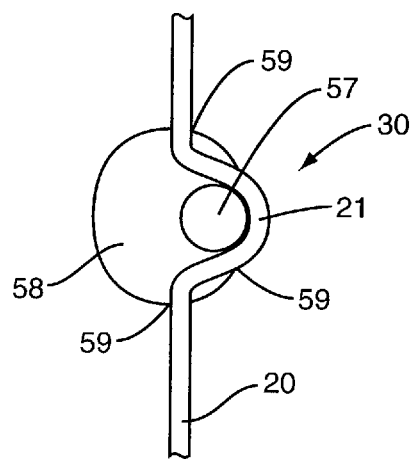
FIG. 10 is a schematic view of a tether within a release mechanism according to one embodiment.

FIG. 10 is a similar embodiment to FIG. 9 with the release mechanism 30 also including a node 57 and an exterior member 58. In this embodiment, the curved section 21 is formed by the tether 20 extending along a limited section of the node 57 (i.e., tether 20 does not form a coil 22). Exterior member 58 extends around and positions the node 57.

Figure 11:
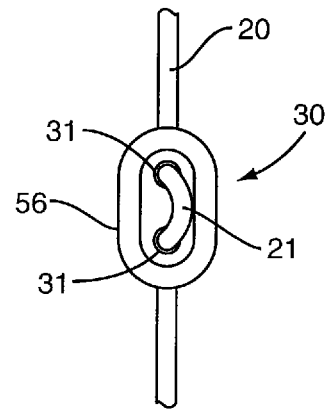
FIG. 11 is a schematic view of a tether within a release mechanism according to one embodiment.

FIG. 11 illustrates another embodiment with the release mechanism 30 includes a button 56 that includes a pair of apertures 31. Tether 20 is threaded through the apertures 31 to form the curved section 21. As the button 56 is absorbed into the body, the curved section 21 straightens causing an increase in the length of the tether 20.

Release mechanism 30 may be formed as a spring 70 with a resorbable portion. The entire spring 70, or a limited section may be constructed of a resorbable material. The spring 70 includes a first spring constant when the resorbable portion is in the first condition. As time progresses, the resorbable material changes to the second condition and changes the spring constant to a more or less rigid condition to address healing or progression of the pathology.

Figure 12:
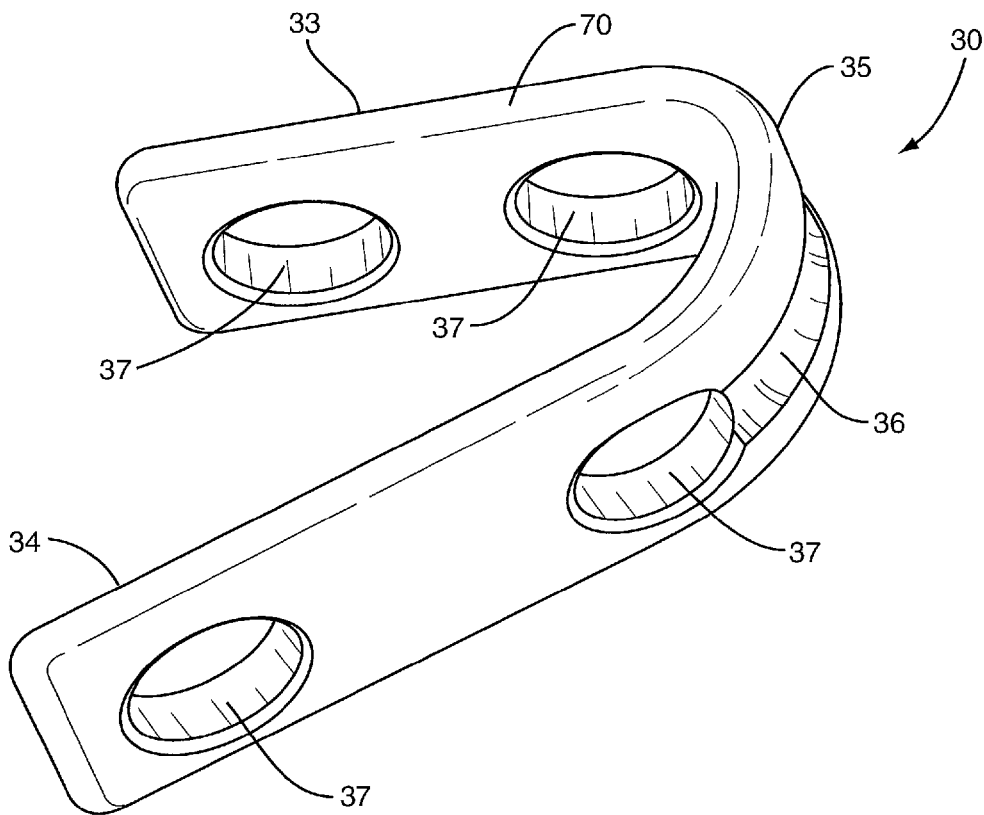
FIG. 12 is a perspective view of release mechanism according to one embodiment.
Figure 13:
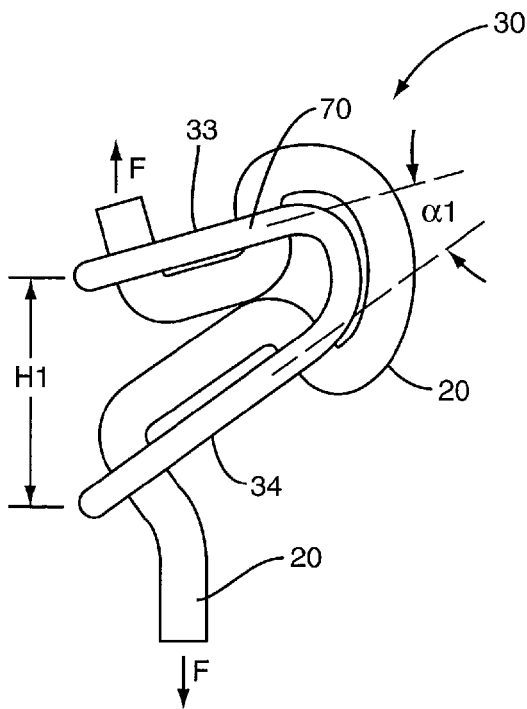
FIG. 13 is a side view of a tether within a release mechanism according to one embodiment.
Figure 14:
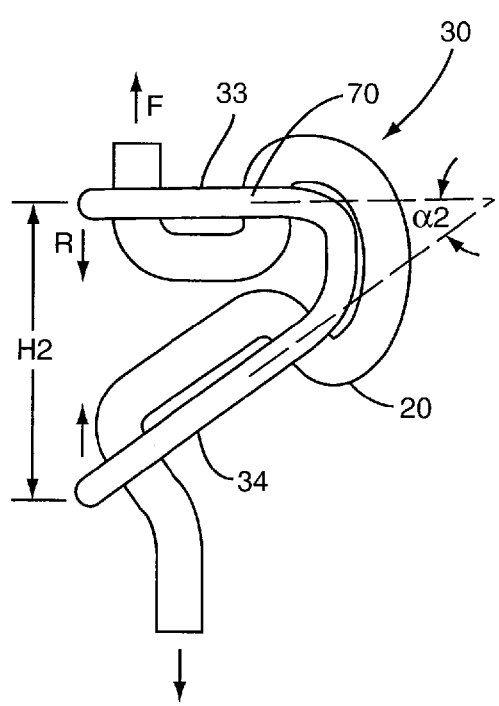
FIG. 14 is a side view of a tether within a release mechanism according to one embodiment.

FIGS. 12-14 illustrate one embodiment with the release mechanism 30 formed as a leaf spring 70. Spring 70 includes first and second arms 33, 34 that extend from an intermediate bend 35. A groove 36 may be disposed along the convex side of the bend 35 and sized to receive the tether 20. Further, each of the first and second arms 33, 34 include apertures 37 sized to accept the tether 20.

FIG. 13 illustrates a lateral view of the spring 70 with the tether 20 threaded through the various apertures 37. The first and second arms 33, 34 are positioned to form a generally acute angle α1. In a first condition shown in FIG. 13, the spring 70 includes a first spring constant such that a force F applied to the tether 20 results in the ends of the arms 33, 34 opposite the bend 35 being spaced apart a distance H1. In a second condition shown in FIG. 14, the same force F applied to the tether 20 results in the first and second arms 33, 34 separating a greater distance H2. In this extended condition shown in FIG. 14, the arms 33, 34 are separated by a greater angle α2, which happens to remain acute in the present embodiment.

Figure 15:
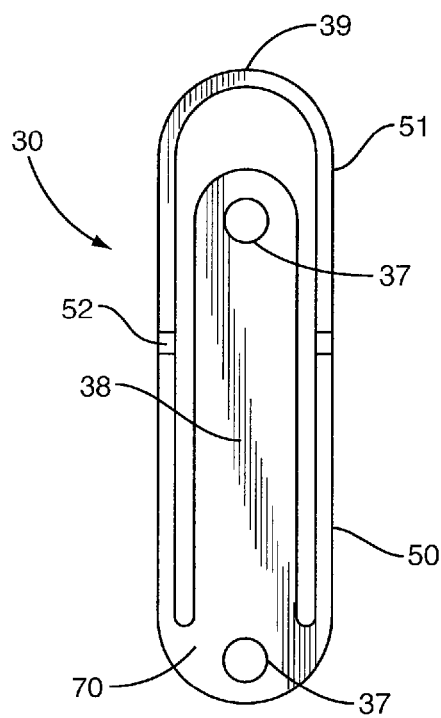
FIG. 15 is a front view of a release mechanism according to one embodiment.
Figure 16:
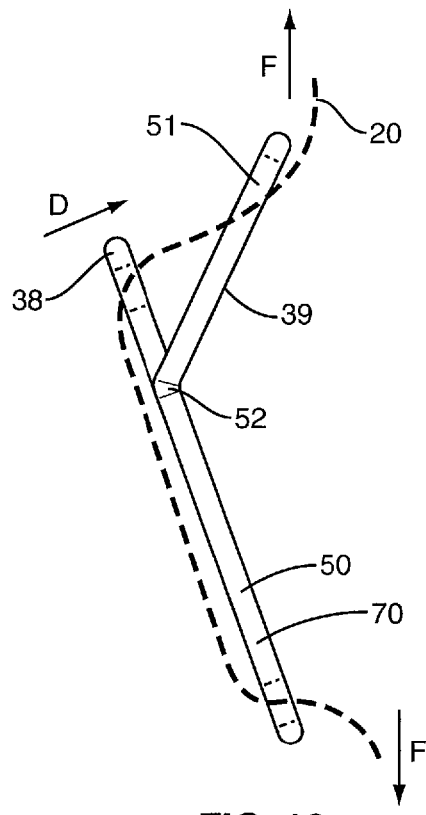
FIG. 16 is a schematic side view of a tether within a release mechanism according to one embodiment.

FIG. 15 shows an embodiment of a spring 70 that includes a cantilevered central arm 38 that is deflectable relative to an arched frame 39. The central arm 38 includes apertures 37 through which the tether 20 may be threaded. FIG. 16 illustrates a side view of the spring 70 from FIG. 15 with a dashed line to indicate attachment of the tether 20. The arched frame 39 comprises an elongated body with first and second arms 50, 51 extending from an intermediate bend 52. A tension force F applied to the tether 20 tends to deflect the central arm 38 in the direction of deflection arrow D.

Figure 17:
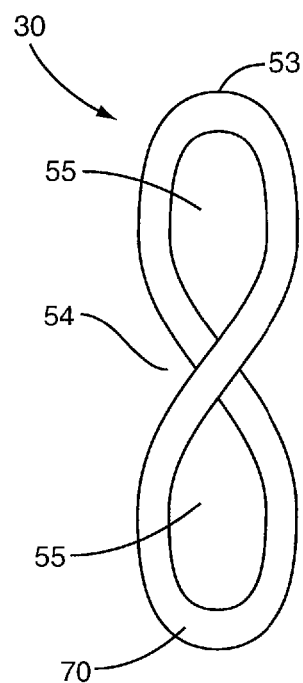
FIG. 17 is a front view of a release mechanism according to one embodiment.
Figure 18:
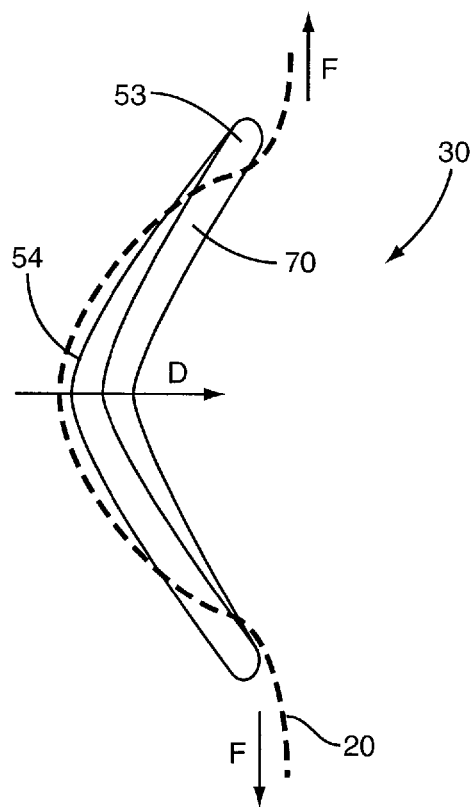
FIG. 18 is a schematic side view of a tether within a release mechanism according to one embodiment.

FIG. 17 illustrates another spring 70 embodiment that includes a wire 53 formed into a loop. In FIG. 17, the looped wire 53 forms a figure eight with the wire crossing at a central junction 54 and forming two tether apertures 55. FIG. 18 illustrates that the looped wire 53 includes an arched configuration with a bend formed at the central junction 54. As FIG. 18 illustrates, a tension force F applied to the tether 20 tends to flatten the looped wire 53 and deflect the central junction 54 in the direction of deflection arrow D.

FIG. 19 illustrates another embodiment of a release mechanism 30 comprising a suture 71 that extends through the tether 20 at two or more locations and forms several curved sections 21. In one embodiment, caps 72 are positioned at the ends of the suture 72 for attachment to the tether 20. Caps 72 may include an enlarged member such as a flange attached to the suture 71 to prevent the suture 71 from pulling through from the tether 20. Caps 72 may also comprise a knot in the suture 71 that include an enlarged size to prevent the suture 71 from pulling through the tether 20. Suture 71 is constructed of a resorbable material that maintains the curved section 21 for a period of time. The suture 71 is eventually absorbed by the body allowing the curved sections 21 to straighten thereby increasing the length of the tether 20 and thus removing tension. FIG. 19 includes a single suture 71 forming multiple curved sections 21. In another embodiment, multiple sutures 71 are attached to the tether 20 each forming one or more curved sections 21.

FIG. 20 illustrates an embodiment with the release mechanism 30 including a plurality of nodes 57. Nodes 57 are attached to the tether 20 to form curved sections 21 that shortening the length. In one embodiment, the nodes 57 are cylindrical with a substantially circular cross-sectional shape. The nodes 57 may be attached to the tether 20 in a variety of manners including adhesives. In one embodiment, a holding member 73 is attached to the tether 20 and forms a pocket to position the node 57. As the nodes 57 absorb into the body, the diameters decrease thus decreasing the size of the curved sections 21 and increasing the length of the tether 20.

FIG. 21 includes a release mechanism 30 formed from a node 57 and a suture 71. Node 57 is positioned to form a curved section 21 in the tether 20. Suture 71 extends across a neck of the curved section 21 to prevent the node 57 from escaping. In one embodiment, both the node 57 and suture 71 are constructed of resorbable materials that are absorbed by the body. The absorption causes the curved section 21 to dissipate and thus increase the overall length of the tether 20.

FIG. 22 includes a release mechanism 30 comprising a gripper mechanism 60 with an aperture 61 to receive the tether 20. Teeth 62 are positioned along a section of the aperture 61 to contact against the tether 20. A roller 63 is movably mounted on the end of a biased pivot arm 64 and positioned opposite from the teeth 62. Tether 20 is positioned through the aperture 61 and the gripper mechanism 60 is moved along the tether 20 in a direction indicated by arrow X to apply an initial tension to the tether 20. The roller 63 is moved against a first side of the tether 20 by a biasing member to force a second side of the tether 20 against the teeth 62 to fix the position of the gripper mechanism 60 along the tether 20 and fix the amount of tension. Either one or both of the teeth 62 and the roller 63 are constructed of resorbable materials. As the materials are absorbed by the body, the tether 20 is able to move relative to the gripper mechanism 60 thus releasing the tension that is originally applied to the tether 20.

FIG. 23 illustrates another embodiment with the release mechanism 30 including a block 84 that extends around the spring 70. Block 84 is constructed of resorbable material that is initially in the first condition and prevents the spring 70 from expanding. The resorbable material 84 eventually changes to the second condition to allow the spring 70 to move and vary the height H formed between the arms 33, 34. In one embodiment, spring 70 is constructed of a non-resorbable material and remains a spring indefinitely within the patient. In another embodiment, spring 70 is constructed of a second, resorbable material that eventually changes to the second condition and increases a length of the tether 20. The embodiment of FIG. 23 includes a leaf spring, although other embodiments may include different spring types such as a coil spring and others.

The various release mechanisms 30 are constructed partially or totally from one or more resorbable materials. These materials are in a first condition when initially placed into the body, and change to a second condition after a period of time within the body. The second condition occurs when the resorbable material has been absorbed an amount to cause the release mechanism 30 to increase the length of the tether 20. In one embodiment, the absorption is a gradual transition from the first condition to the second condition. In another embodiment, the absorption results in a discrete second condition, such as absorption of the entire material causing an abrupt transition to the second condition. In one embodiment, the change to the second condition may cause the release mechanism 30 to slowly increase the length of the tether 20. By way of example, the block 84 of FIG. 6 and node 57 of FIGS. 9 and 10 may slowly absorb thus causing the length of the tether 20 to slowly increase. In another embodiment, the change to the second condition may cause a sudden increase in the length of the tether 20. By way of example, the blocks 84 of FIGS. 7 and 8, and the suture 71 of FIG. 19 may absorb to an amount that suddenly releases the curved section or sections 21 of the tether 20. Since the resorbable materials can be programmed to absorb over an extended time after being inserted within the patient, the tension in the tether 20 may be reduced or removed without the need to perform a subsequent surgical procedure.

Each of the resorbable materials is absorbed into the body within a period of time which is generally indicated as a resorption rate. A greater rate indicates that the material is absorbed in the body faster than a material with a slower absorption rate. By way of example, polyglycolide (PGA—resorption time of about 4-6 weeks) includes a greater absorption rate than poly L-lactide (PLLA—resorption time as long as 5 years). Selection of the necessary resorbable materials for the release mechanisms 30 may be based on the required timing for treating the specific deformity of the bony members 90. In one embodiment, the resorbable materials may change to the second condition to release the tether 20 after a relatively short period of time after being implanted, such as two or three months. In one embodiment, the resorbable materials change to the second condition after years of being implanted.

In one embodiment, the various release mechanisms 30 are constructed of a single resorbable material. FIG. 6 illustrates an example of the block 84 constructed of a single, resorbable material. In another embodiment, release mechanism 30 is constructed of at least two different resorbable materials. FIG. 24 schematically illustrates one embodiment of a release mechanism 30 constructed of a first resorbable material 40 and a second resorbable material 41. The materials 40, 41 may include different resorption rates that in combination affect the overall release of the curved section 21. In one embodiment, the outer, first material 40 may include a greater absorption rate than the inner, second material 41. Outer material 40 may also act as a shield to prevent bodily fluid that may cause absorption from contacting the second material 41. This first material 40 acts as a shield for a given period of time before being absorbed and allowing the bodily fluid to contact the second material 41. FIG. 24 schematically represents two separate resorbable materials, 40, 41, although it is to be understood that more than two resorbable materials may also be used to construct the release mechanism 30.

Release mechanism 30 may also include resorbable materials in combination with non-resorbable materials. FIG. 25A illustrates a release mechanism 30 comprising a node 57 constructed of a first resorbable material 40 and a non-resorbable material 42. As illustrated in FIG. 25A, the node 57 includes a first diameter to form an enlarged curved section 21 and giving the tether 20 a length L. Resorbable material 40 is absorbed by the body after a period of time leaving the node 57 to just include the non-resorbable material 42. This causes the node 57 to include a reduced diameter such that the curved section 21' remains but is now smaller. The smaller node 57 also causes the tether 20 to increase to length L'. FIGS. 25A and 25B illustrate a release mechanism with a single resorbable material 40 in combination with a single non-resorbable material 42. It is understood that other embodiments may feature multiple resorbable and/or multiple non-resorbable materials.

The resorption rates of the resorbable materials may be altered in a number of different methods. A first method includes shielding the resorbable material from the bodily fluids. One embodiment is illustrated in FIG. 24 and discussed above with the second resorbable material 41 being shielded by the first resorbable material 40. FIGS. 9 and 10 illustrate another embodiment with an exterior member 58 extending around and shielding the resorbable material. Exterior member 58 may be constructed of a resorbable material, or of a non-resorbable material. The shields may also function to position the resorbable material relative to the tether 20. By way of example, exterior member 58 of FIG. 9 positions the node 57 against the tether 20. Shields may also prevent the ingrowth of tissue that could prevent the release mechanism 30 from releasing the tether 20. In another embodiment, integrally molding the release mechanism 30 to the tether 20 may create a shield that affects contact of the bodily fluid with the release mechanism 30.

Another method of controlling the resorption rate is to position openings 59 to increase the amount of bodily fluid contact with the resorbable material. FIG. 23 includes an embodiment with an opening 59 through the outer, first material 40 and into the inner, second material 41. The opening 59 causes the second material 41 to begin changing to the second condition in a shorter period of time than if the opening 59 was not present. FIGS. 9 and 10 include openings 59 leading to the resorbable materials nodes 57. The openings 59 of FIG.

10 are limited to inlets for positioning the tether 20. FIG. 9 includes the inlets, in addition to a separate opening 59 positioned away from the tether 20.

The release mechanism 30 may be positioned at various locations along the construct. In one embodiment, release mechanism 30 is operatively connected to one of the anchors 80. In another embodiment, release mechanism 30 is attached to the tether 20 between the anchors 80. In yet another embodiment, release mechanism 30 is positioned outside of the anchors 80.

Release mechanism 30 may be constructed from a variety of resorbable materials including but not limited to polylactide, poly-L-lactide, poly-D-lactide, polyglycolide, tyrosine-derived polycarbonate, polyanhydride, polyorthoester, polyphosphazene, calcium phosphate, hydroxyapatite, bioactive glass, collagen, albumin, fibrinogen, polylactide-co-glycolide (PLGA), poly-L-lysine and combinations thereof. A variety of non-resorbable materials may also be included in the release mechanisms 30. Examples include stainless steel, titanium, Nitinol, cobalt chrome, polyethyelene, polyester, and polyetheretherketone (PEEK).

Figure 26:
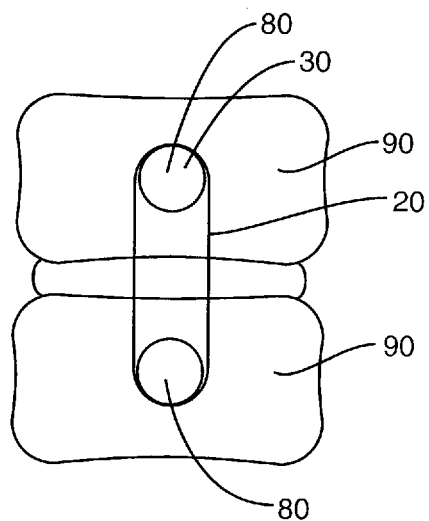
FIG. 26 is a schematic view of a tether with a release mechanism according to one embodiment.
Figure 27:
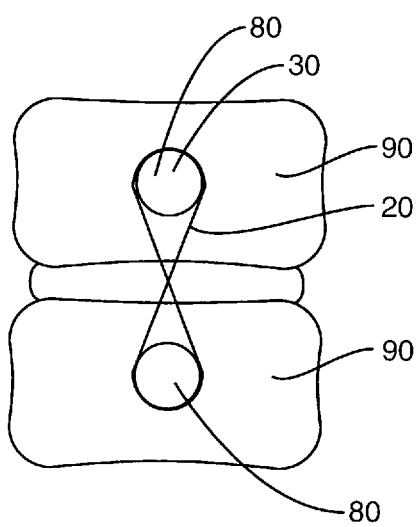
FIG. 27 is a schematic view of a tether with a release mechanism according to one embodiment.

Tether 20 may also include a looped configuration as illustrated in FIGS. 26 and 27. FIG. 26 includes a circular tether 20 that extends around the anchors 80 positioned in adjacent bony members 90. FIG. 27 includes a cross-over looped tether 20 that has a shape roughly corresponding to a FIG. 8. The release mechanisms 30 for the looped configurations may be positioned at various locations as described above. In these specific embodiments, the release mechanisms 30 are constructed within the anchors 80.

Figure 28:
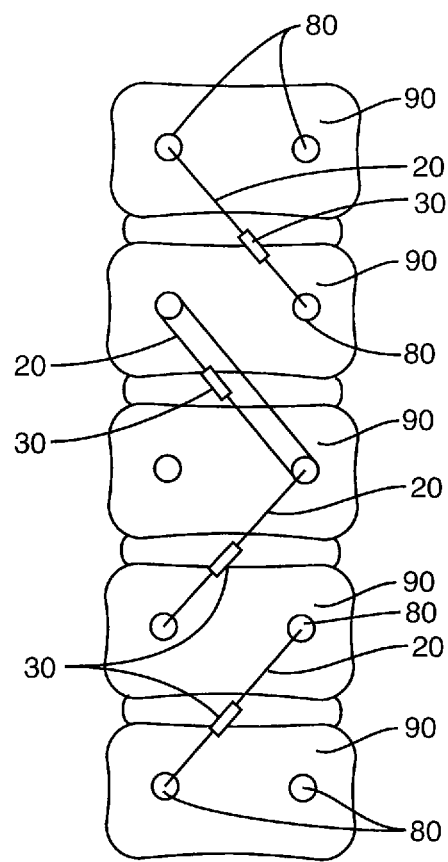
FIG. 28 is a schematic view of a tether with a release mechanism according to one embodiment.

FIG. 28 illustrates another embodiment of a tethering system that uses multiple tethers 20 for derotation of a deformity. The various tethers 20 span diagonally between the bony members 90. Each of the tethers 20 may work in combination to treat the over deformity of the plurality of bony members 90.

Figure 29:
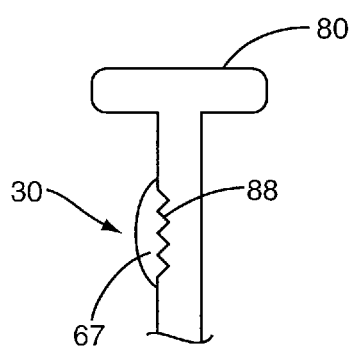
FIG. 29 is a partial side view of an anchor with a cutting edge according to one embodiment.
Figure 30:
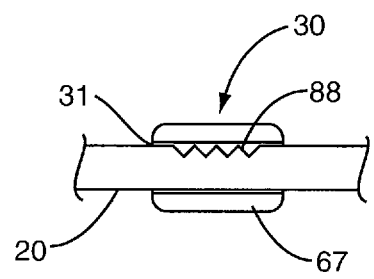
FIG. 30 is a schematic view of a tether with a release mechanism according to one embodiment.

The release mechanism 30 may further include a cutting mechanism to cut the tether 20 after a period of time of being implanted within the patient. FIG. 29 illustrates one embodiment with an anchor 80 including a cutting edge 88. A shield 67 constructed of a resorbable material extends over the cutting edge 88 when in the first condition. The tether (not illustrated in FIG. 29 for purposes of clarity) extends over the shield 67 and cutting edge 88. In the first condition, the shield 67 spaces the tether 20 away from the cutting edge 88. In the second condition, the tether 20 contacts the cutting edge 88 eventually causing the tether 20 to be cut and release the tension. FIG. 30 illustrates another embodiment with the tether 20 extending through an aperture 31 in a block 84. A cutting edge 88 is positioned within the aperture 31. A shield 67 is initially placed over the cutting edge 88 to prevent contact between the edge 88 and the tether 20 with the shield 67 in a first condition. Upon changing to the second condition, tether 20 contacts the cutting edge 88 and eventually cuts the tether 20.

Figure 31:
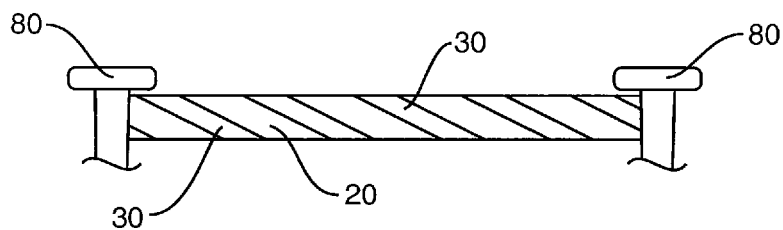
FIG. 31 is a schematic view of a tether with a release mechanism according to one embodiment.

FIG. 31 illustrates another embodiment with a tether 20 extending between anchors 80. A resorbable release mechanism 30 extends directly between the anchors 80. A non-resorbable tether 20 is wrapped around the release mechanism 30 and thus includes a greater length than the tether 20. In this embodiment, the release mechanism 30 initially bears the tension because of the shorter length. Eventually, the release mechanism 30 releases and the tension is received by the longer tether 20. In one specific embodiment, the tension is gradually transitioned to the lengthened tether 20.

Figure 32C:
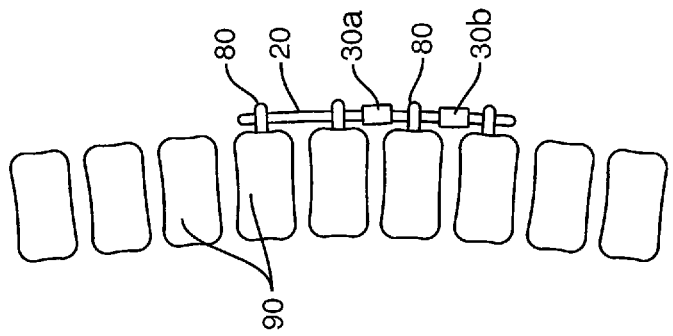
FIG. 32C is a schematic side view of a tethering system attached to bony members at a third period of time according to one embodiment.
Figure 32B:
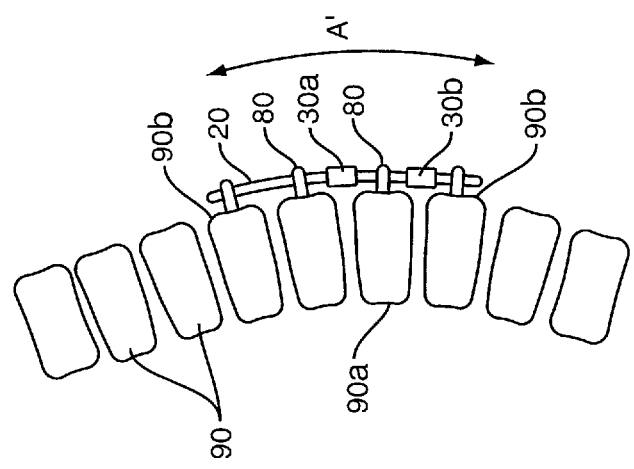
FIG. 32B is a schematic side view of a tethering system attached to bony members at a second period of time according to one embodiment.
Figure 32A:
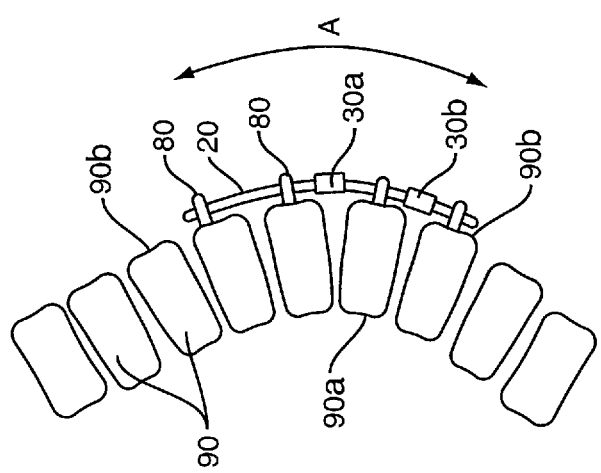
FIG. 32A is a schematic side view of a tethering system attached to bony members at a first period of time according to one embodiment.

FIGS. 32A-32C illustrate one embodiment of the tethering system for use in treating a spinal deformity. FIG. 32A illustrates the tether 20 attached to the convex side 90b of the vertebral members 90. In one embodiment, the tether 20 is placed in tension as illustrated by arrow A when initially connected to the anchors 20. In another embodiment, tether 20 is not in tension when initially connected to the anchors 20.

FIG. 32B illustrates the tethering system at a period of time after initially attached inserted within the patient. The growth of the vertebral members 90 allows the untethered concave side of the spine to grow unconstrained which reduces the curvature of the spine in the coronal plane. The growth also increases the amount of tensile force applied to the tether 20. At some period of time after the tethering system is placed in the system, one or both release mechanisms 30a, 30b increase the length of the tether 20. In one embodiment, the first release mechanism 30a initially increases the length and then the second release mechanism 30b increases the length at a later period of time. In another embodiment, both increase the length of the tether 20 concurrently. The increase in the length reduces the amount to tension applied to the tether 20 by the growing vertebral members 90.

FIG. 32C illustrates the tether 20 at a later period of time than that of FIG. 26B. The release mechanisms 30 have caused the length of the tether 20 to increase to prevent tensile force applied to the tether 40 from either preventing or slowing the growth of the vertebral members 90, or damaging the vertebral members or intervertebral discs. The placement of the tethering system on the vertebral members 90 results in the spinal deformity being reduced or eliminated as the vertebral members 90 are more substantially aligned than the previous orientations.

The above embodiments may be used to treat a wide range of spinal deformities. The primary indications will be progressive idiopathic scoliosis with or without sagittal deformity in either infantile or juvenile patients. One patient population upon which to practice these embodiments is prepubescent children (before growth spurt) less than ten years old. Other patient groups upon which the embodiments may be practiced include adolescents from 10-12 years old with continued growth potential. It should be understood that fusionless tethering may also be used on older children whose growth spurt is late or who otherwise retain growth potential. It should be further understood that fusionless tethering may also find use in preventing or minimizing curve progression in individuals of various ages.

Generally, in the case of scoliosis, tethering will take place on the convex side of the curve. In one embodiment, the tether 20 is implanted with an anterior, minimally invasive (thoracoscopic) procedure on the convex side of the spinal curve. The tether 20 may be delivered into the patient in a minimally invasive approach using thoracoscopic instrumentation. The tether 20 may also be delivered in a posterior procedure, or some combination of both anterior and posterior. Finally, it should be understood that if the procedure fails to correct the curve but does, in fact, prevent further progression (which includes increase in the magnitude of the curve) it can and should be considered successful.

It should be understood that scoliosis is but one of many types of spinal deformities that can be addressed by the devices and techniques of the present application. Most commonly the devices and methods are expected to be used for either primary thoracic or thoracolumbar curves. They can be used for correction of the thoracic curve as an isolated curve, or the lumbar curve as an isolated curve.

The devices and methods may be used to treat spinal deformities in the coronal plane, such as a scoliotic spine illustrated in FIG. 2. The devices and methods may also be used to treat deformities in the sagittal plane, such as a kyphotic spine or Scheurmann's kyphosis.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. In one embodiment, the geometry of the release mechanism 30 is established to expose a predetermined amount of surface area to the physiologic environment thus controlling the release timing. The present embodiments are, therefore, to be considered in all respects as illustrative and not restrictive, and all changes coming within the meaning and equivalency range of the appended claims are intended to be embraced therein.

What is claimed is:

1. A method of treating a deformity in bony members comprising:
    attaching a tether to a first bony member with a first anchor;
    attaching the tether to a second bony member with a second anchor;
    positioning a release mechanism comprising an absorbable button having apertures operatively connected to the tether by threading the tether through the apertures to form a curved section between the apertures, said release mechanism is positioned between the first and second anchors such that a length of the tether remains substantially constant until the release mechanism absorbs into the body; and
    after the tether has been attached to the first and second anchors for an extended period of time, the release mechanism is absorbed into the body causing the tether to straighten and increase in length between the first and second anchors while the tether and release mechanism are in situ and as the release mechanism is absorbed into the body.

2. The method of claim 1, wherein the step of causing the release mechanism to increase the length of the tether between the first and second anchors comprises releasing the curved section of the tether as the release mechanism is absorbed into the body.

3. The method of claim 1, further comprising extending the tether diagonally between the bony members to correct a rotational deformity of the bony members.

4. A method of treating a deformity in bony members comprising:
    attaching a tether with a release mechanism comprising a button having apertures, to first and second bony members such that a length of the tether remains substantially constant until the release mechanism is absorbed into the body;
    while the release mechanism is in situ, causing the release mechanism to gradually release a curved section of the tether and increasing the length of the tether between the first and second bony members as the release mechanism is being absorbed into the body.

* * * * *